(12) United States Patent
Gosal et al.

(10) Patent No.: US 10,368,986 B2
(45) Date of Patent: Aug. 6, 2019

(54) TRANSCATHETER PROSTHETIC HEART VALVE DELIVERY SYSTEM AND METHOD

(71) Applicant: Medtronic, Inc., Minneapolis, MN (US)

(72) Inventors: Devin Gosal, Santa Rosa, CA (US); Susheel Deshmukh, Santa Rosa, CA (US); Philip Haarstad, Minneapolis, MN (US); Joel Racchini, Edina, MN (US); Finn Rinne, Santa Rosa, CA (US); Paul Rothstein, Elk River, MN (US); Jeffrey Sandstrom, Scandia, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 516 days.

(21) Appl. No.: 14/687,295

(22) Filed: Apr. 15, 2015

(65) Prior Publication Data

US 2016/0302921 A1    Oct. 20, 2016

(51) Int. Cl.
*A61F 2/24*    (2006.01)
*A61F 2/95*    (2013.01)

(52) U.S. Cl.
CPC .......... *A61F 2/2427* (2013.01); *A61F 2/2418* (2013.01); *A61F 2/2436* (2013.01);
(Continued)

(58) Field of Classification Search
CPC .... A61F 2/2427; A61F 2/2418; A61F 2/2436; A61F 2230/001; A61F 2250/0039; A61F 2002/9522
See application file for complete search history.

(56) References Cited

U.S. PATENT DOCUMENTS

2006/0206192 A1    9/2006    Tower et al.
2006/0265056 A1    11/2006    Nguyen et al.
(Continued)

FOREIGN PATENT DOCUMENTS

WO    WO2007/120543    10/2007
WO    WO2008/070797    6/2008
(Continued)

OTHER PUBLICATIONS

PCT/US2016/026559, The International Search Report and the Written Opinion of the International Searching Authority.

*Primary Examiner* — Katrina M Stransky
*Assistant Examiner* — Michael G Mendoza
(74) *Attorney, Agent, or Firm* — Medler Ferro Woodhouse & Mills PLLC

(57) ABSTRACT

A system for percutaneous delivery of a stented prosthetic heart valve. The system includes a delivery device with a self-expanding prosthetic heart valve attached thereto and a delivery sheath with an opening on a distal end thereof. The delivery sheath includes a funnel on a proximal end thereof. The delivery device is inserted into the funnel of the delivery sheath. As the delivery device is advanced into the funnel, the expanded heart valve is compressed by the shape of the funnel into a crimped arrangement. The delivery device further advances the heart valve distally within the delivery sheath past the delivery sheath opening. The delivery device is advanced relative to the delivery sheath in transitioning the heart valve from a crimped arrangement to the expanded and deployed arrangement.

6 Claims, 14 Drawing Sheets

(52) U.S. Cl.
CPC . *A61F 2002/9522* (2013.01); *A61F 2230/001* (2013.01); *A61F 2250/0039* (2013.01)

(56) References Cited

U.S. PATENT DOCUMENTS

| | | | |
|---|---|---|---|
| 2007/0239266 A1 | 10/2007 | Birdsall | |
| 2007/0239269 A1 | 10/2007 | Dolan et al. | |
| 2007/0239271 A1* | 10/2007 | Nguyen | A61F 2/2436 623/2.11 |
| 2007/0288000 A1* | 12/2007 | Bonan | A61B 6/481 606/46 |
| 2011/0208296 A1 | 8/2011 | Duffy et al. | |
| 2011/0251679 A1 | 10/2011 | Wiemeyer et al. | |
| 2011/0251683 A1 | 10/2011 | Tabor | |
| 2011/0257733 A1 | 10/2011 | Dwork | |
| 2011/0264133 A1 | 10/2011 | Hanlon et al. | |
| 2011/0282425 A1 | 11/2011 | Dwork | |
| 2012/0209375 A1 | 8/2012 | Madrid et al. | |
| 2012/0310332 A1 | 12/2012 | Murray et al. | |
| 2012/0330408 A1* | 12/2012 | Hillukka | A61F 2/0095 623/2.11 |
| 2013/0190859 A1* | 7/2013 | Hillukka | A61F 2/2427 623/2.11 |

FOREIGN PATENT DOCUMENTS

| | | |
|---|---|---|
| WO | WO2012/106491 | 8/2012 |
| WO | WO2012/116368 | 8/2012 |
| WO | WO2013/016549 | 1/2013 |
| WO | WO2013/177684 | 12/2013 |

* cited by examiner

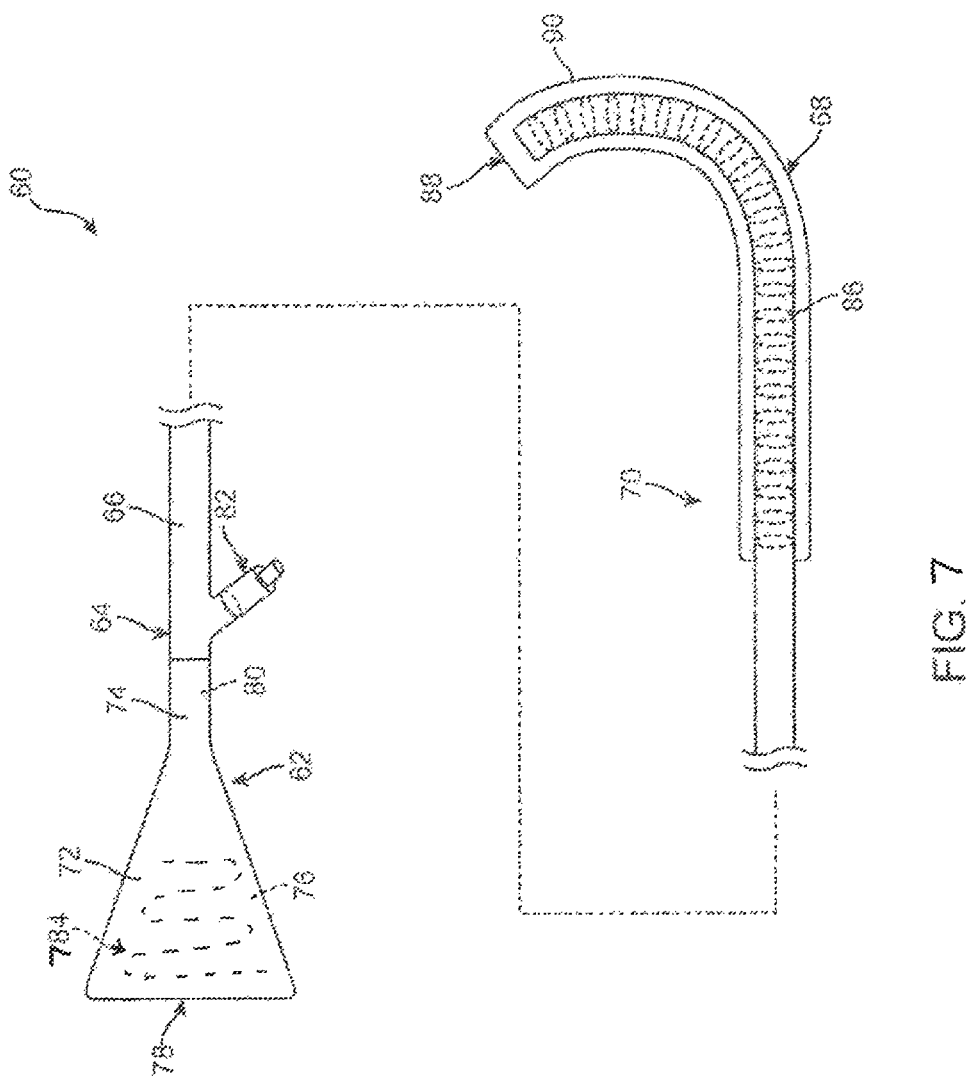

TRANSCATHETER PROSTHETIC HEART VALVE DELIVERY SYSTEM AND METHOD

BACKGROUND

The present disclosure relates to systems and methods for percutaneous implantation of a prosthetic heart valve. More particularly, it relates to systems and methods for transcatheter implantation of a stented prosthetic heart valve.

Diseased or otherwise deficient heart valves can be repaired or replaced with an implanted prosthetic heart valve. As used throughout this specification, the terms "repair," "replace," and "restore" are used interchangeably, and reference to "restoring" a defective heart valve is inclusive implanting a prosthetic heart valve that renders the native leaflets non-functional, or that leaves the native leaflets intact and functional. Conventionally, heart valve replacement surgery is an open-heart procedure conducted under general anesthesia, during which the heart is stopped and blood flow is controlled by a heart-lung bypass machine. Traditional open surgery inflects significant patient trauma and discomfort, and exposes the patient to a number of potential risks, such as an infection, stroke, renal failure, and adverse affects associated with the use of the heart-lung machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be repaired (e.g., the aortic valve annulus). Although transcatheter techniques have attained widespread acceptance with respect to delivery of conventional stents to restore vessel patency, only mixed results have been realized with respect to percutaneous delivery of the more complex prosthetic heart valve.

Various types and configurations of prosthetic heart valves are available for percutaneous valve replacement procedures, and continue to be refined. The actual shape and configuration of any particular prosthetic heart valve is dependent to some extent upon the native shape and size of the valve being replaced or repaired (i.e., mitral valve, tricuspid valve, aortic valve, or pulmonary valve). In general, prosthetic heart valve designs attempt to replicate the function of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation devices, the stent frame of the valved stent can be made of a self-expanding material and construction. With these devices, the valved stent is crimped down to a desired size and held in that compressed state within an outer delivery sheath, for example. Retracting the sheath from the valved stent allows the stent to self-expand to a larger diameter, such as when the valved stent is in a desired position within a patient. In other percutaneous implantation systems the valved stent can be initially provided in an expanded or uncrimped condition, then crimped or compressed on a balloon portion of a catheter until it is as close to the diameter of the catheter as possible. Once delivered to the implantation site, the balloon is inflated to deploy the prosthesis. With either of these types of percutaneous stented prosthetic valve delivery devices, conventional sewing of the prosthetic heart valve to the patient's native tissue is typically not necessary.

In addition to the delivery device itself, typical transcatheter heart valve implantation techniques entail the use of a separate introducer device to establish a portal to the patient's vasculature (e.g., femoral artery) and through which the prosthetic valve-loaded delivery device is inserted. The introducer device generally includes a relatively short sheath and a valve structure.

For example, FIG. 1A illustrates, in simplified form, an introducer device 10 establishing a portal to a patient's vasculature 12, and through which a prosthetic heart valve-loaded delivery shaft 14 (the tip of which is visible in FIG. 1A) has been inserted. As shown, the delivery shaft 14 has been manipulated to locate the loaded prosthetic heart valve 16 (referenced generally) in a desired position relative to an aortic valve 18. An outer delivery sheath 20 contains the prosthesis 16. Thus, in the state of FIG. 1A, the prosthetic heart valve 16 is properly positioned for deployment from the delivery shaft 14 upon proximal retraction of the delivery sheath 20 relative thereto, with a spacing S being established between a distal end of the delivery device's handle 22 and the introducer device 10. As shown in FIG. 1B, an actuator 24 of the handle 22 is moved by the clinician to proximally pull or retract the delivery sheath 20 (as shown by arrow B in FIG. 1B) and release the prosthesis 16.

In light of the above, although there have been advances in percutaneous valve replacement techniques and devices, there is a continued desired to provide different delivery systems for delivering cardiac replacement valves, and in particular self-expanding stented prosthetic heart valves, to an implantation site in a minimally invasive and percutaneous manner.

SUMMARY

The delivery systems of the present disclosure can be used to deliver replacement valves to the heart of a patient. These replacement heart valves may be configured to provide complementary features that promote optimal placement of the replacement heart valve in a native heart valve, such as the aortic valve, mitral valve, pulmonic valve, and/or tricuspid valve. In some embodiments, the replacement heart valves of the present disclosure are highly amenable to transvascular delivery using retrograde transarterial approach (either with or without rapid pacing). The methodologies associated with the present disclosure can be repeated multiple times, such that several prosthetic heart valves of the present disclosure can be mounted on top of, adjacent to, or within one another, if necessary or desired.

The replacement heart valves that are delivered using the systems and methods of the present disclosure typically include a stent frame to which a valve structure is attached. These stent frames can include a wide variety of structures and features that can be used alone or in combination with features of other stent frames. In particular, these stent frames provide a number of different docking and/or anchoring structures that are conducive to percutaneous delivery thereof. Many of the structures are thus compressible to a relatively small diameter for percutaneous delivery to the heart of the patient, and then are expandable via removal of external compressive forces (i.e., self-expanding stents). The device is delivered by the delivery systems described herein can be used to deliver stents, valved stents, or other interventional devices such as ASD (atrial septal defect) closure devices, VSD (ventricular septal defect) closure devices, or PFO (patent foramen ovale) occluders.

Yet other aspects in accordance with principles of the present disclosure relate to a system for restoring a heart valve of a patient, and include a delivery device along with a prosthetic heart valve. The prosthetic heart valve has a stent frame and a valve structure attached to the frame and forming at least two valve leaflets. The prosthetic heart valve is self-expandable from a compressed arrangement to a natural arrangement. The delivery sheath has a funnel shaped loading cone member at a proximal end to receive the heart valve therein. As the delivery device is advanced into the infundibular loading cone, the heart valve is compressed into a crimped arrangement by the shape of the cone. As the delivery device is further advanced into the delivery sheath, the heart valve is retained within the delivery sheath assembly until the heart valve is advanced past the distal opening of the delivery sheath to permit the prosthesis to self-expand to the natural arrangement and be released from the delivery device. In this regard, the actuator mechanism is configured to effectuate transitioning from the compressed condition to the deployed condition by sliding the delivery device assembly relative to the delivery sheath.

Yet other aspects in accordance with principles of the present disclosure relate to a method for restoring a defective heart valve of a patient. The method includes receiving a delivery device with a prosthetic heart valve having a self-expanding stent frame to which a valve structure is attached. A portal to a bodily lumen of the patient is established by an introducer device including an introducer device. The delivery sheath is inserted into the bodily lumen through the introducer device. In this regard, hemostasis is established between the introducer device and the delivery sheath. The delivery sheath is manipulated through the patient's vasculature and into the defective heart valve. The delivery sheath has an infudibular or funnel shaped loading cone/crimping member at a proximal end to receive the heart valve therein. The delivery device with the heart valve thereon is inserted into the loading cone of the delivery sheath. As the delivery device is advanced into the funnel, the heart valve is compressed into a crimped arrangement by the loading cone. As the delivery device is further advanced into the delivery sheath, the heart valve is retained within the delivery sheath assembly until the heart valve is advanced past the distal opening of the delivery sheath to permit the prosthesis to self-expand to the natural into engagement with tissue of the native heart valve.

BRIEF DESCRIPTION OF THE DRAWINGS

FIG. 7 is an exploded perspective view of a crimping sheath according to another embodiment hereof.

DETAILED DESCRIPTION

Figure 1A:
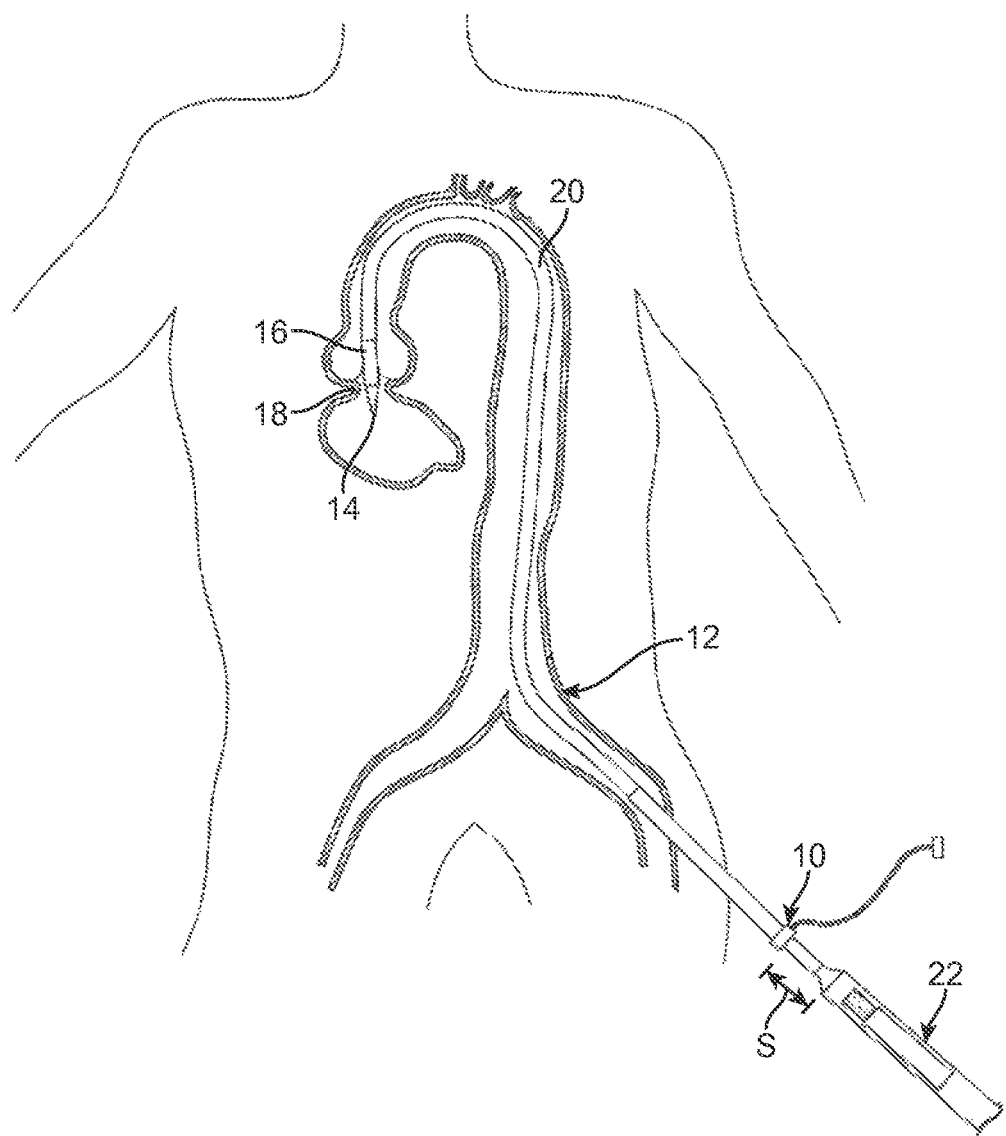
FIGS. 1A and 1B are simplified illustrations of conventional transcatheter delivery and implantation of a stented prosthetic heart valve.
Figure 1B:
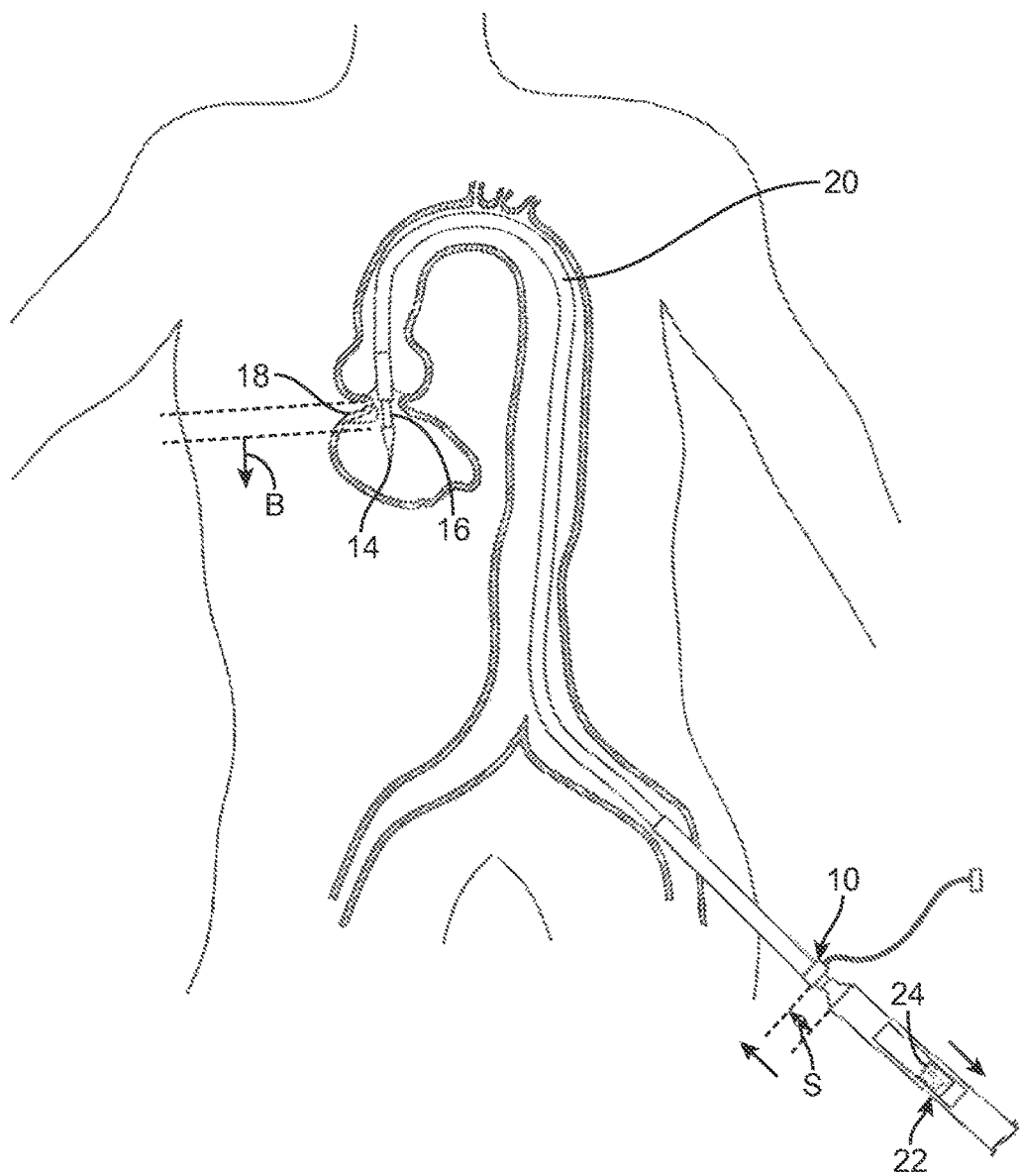

Specific embodiments of the present invention are now described with reference to the figures, wherein like reference numbers indicate identical or functionally similar elements. The terms "distal" and "proximal" are used in the following description with respect to a position or direction relative to the treating clinician when describing an object or device manipulated by the clinician. "Distal" and "distally" are positions distant from or in a direction away from the clinician. "Proximal" and "proximally" are positions near or in a direction toward the clinician. The terms "distal" and "proximal", when used with respect to a position in a vessel refer to a position or direction relative to the direction of blood flow. Accordingly, "distal" and "distally" are positions downstream of a reference position, and "proximal" and "proximally" are positions upstream of the reference position.

The following detailed description of a prosthetic heart valve delivery system refers to the accompanying figures that illustrate exemplary embodiments. Other embodiments are possible. Modifications can be made to the embodiments described herein without departing from the spirit and scope of the present invention. Therefore, the following detailed description is not meant to be limiting. Furthermore, there is no intention to be bound by any expressed or implied theory presented in the preceding technical field, background, brief summary or the following detailed description. As referred to herein, the stented prosthetic heart valves used in accordance with and/or as part of the various systems, devices, and methods of the present disclosure may include a wide variety of different configurations, such as a bioprosthetic heart valve having tissue leaflets or a synthetic heart valve having polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

In general terms, the stented prosthetic heart valves of the present disclosure include a stent maintaining a valve structure (tissue or synthetic), with the stent having a normal, expanded arrangement and collapsible to a compressed arrangement for loading within the delivery device. The stent is normally constructed to self-deploy or expand when released from the delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2006/0206192; 2007/0239266; 2007/0239269; 2011/0208296; 2011/0251679; 2011/0251683; 2011/0257733; 2011/0264133; 2011/0282425 and 2012/0310332. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine pericardial leaflets) and subsequently assembled to the support structure of the stent frame. In another alternative, the stent frame and leaflets can be fabricated at the same time, such as may be accomplished using high-strength nano-manufactured NiTi films produced at Advanced Bioprosthetic Surfaces (ABPS), for example. The stent frame support structures are generally configured to accommodate at least two (typically three) leaflets; however, replacement prosthetic heart valves of the types described herein can incorporate more or less than three leaflets.

Some embodiments of the stent frames can be a series of wires or wire segments arranged such that they are capable of self-transitioning from the compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached valves can be mounted onto a delivery device. The stent frame support structures are configured so that they can be changed to their normal, expanded arrangement when desired, such as by the relative movement of one or more sheaths relative to a length of the stent frame.

The wires of the support structure of the stent frames in embodiments of the present disclosure can be formed from a shape memory material such as a nickel titanium alloy (e.g., Nitinol). With this material, the support structure is self-expandable from the compressed arrangement to the normal, expanded arrangement, such as by the application of heat, energy, and the like, or by the removal of external forces (e.g. compressive forces). This stent frame support structure can also be compressed and re-expanded multiple times without significantly damaging the structure of the stent frame. In addition, the stent frame support structure of such an embodiment may be laser-cut from a single piece of material or may be assembled from a number of different components or manufactured from a various other methods known in the art. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 2A:
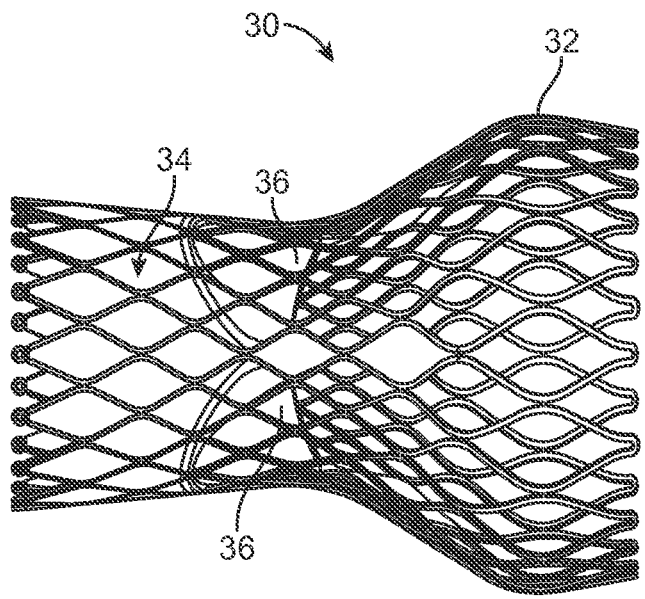
FIG. 2A is a side view of a stented prosthetic heart valve useful with systems, devices, and methods of the present disclosure and in a normal, expanded arrangement.
Figure 2B:
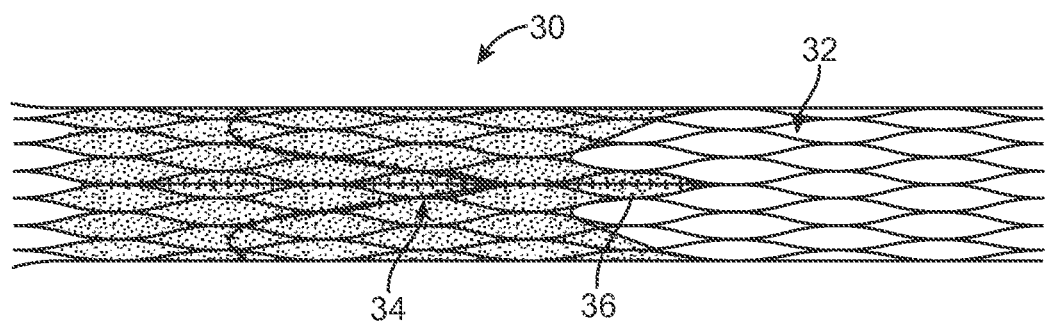
FIG. 2B is a side view of the prosthetic heart valve of FIG. 2A in a compressed arrangement.

With the above understanding in mind, one non-limiting example of a stented prosthetic heart valve 30 useful with systems, devices and methods of the present disclosure is illustrated in FIG. 2A. As a point of reference, the prosthetic heart valve 30 is shown in a normal or expanded arrangement in the view of FIG. 2A; FIG. 2B illustrates the prosthetic heart valve 30 in a compressed arrangement (e.g., when compressively retained within an outer catheter or sheath). The prosthetic heart valve 30 includes a stent or stent frame 32 and a valve structure 34. The stent frame 32 can assume any of the forms described above, and is generally constructed so as to be self-expandable from the compressed arrangement (FIG. 2B) to the normal, expanded arrangement (FIG. 2A). In other embodiments, the stent frame 32 is expandable to the expanded arrangement by a separate device (e.g., a balloon internally located within the stent frame 32). The valve structure 34 is assembled to the stent frame 32 and provides two or more (typically three) leaflets 36. The valve structure 34 can assume any of the forms described above, and can be assembled to the stent frame 32 in various manners, such as by sewing the valve structure 34 to one or more of the wire segments defined by the stent frame 32.

The prosthetic heart valve 30 of FIGS. 2A and 2B is configured for replacing or repairing an aortic valve. Alternatively, other shapes are also envisioned, adapted to the specific anatomy of the valve to be repaired (e.g., stented prosthetic heart valves in accordance with the present disclosure can be shaped and/or sized for replacing a native mitral, pulmonic, or tricuspid valve). With the one construction of FIGS. 2A and 2B, the valve structure 34 extends less than the entire length of the stent frame 32, but in other embodiments can extend along an entirety, or a near entirety, of a length of the stent frame 32. A wide variety of other constructions are also acceptable and within the scope of the present disclosure. For example, the stent frame 32 can have a more cylindrical shape in the normal, expanded arrangement.

Figure 3:
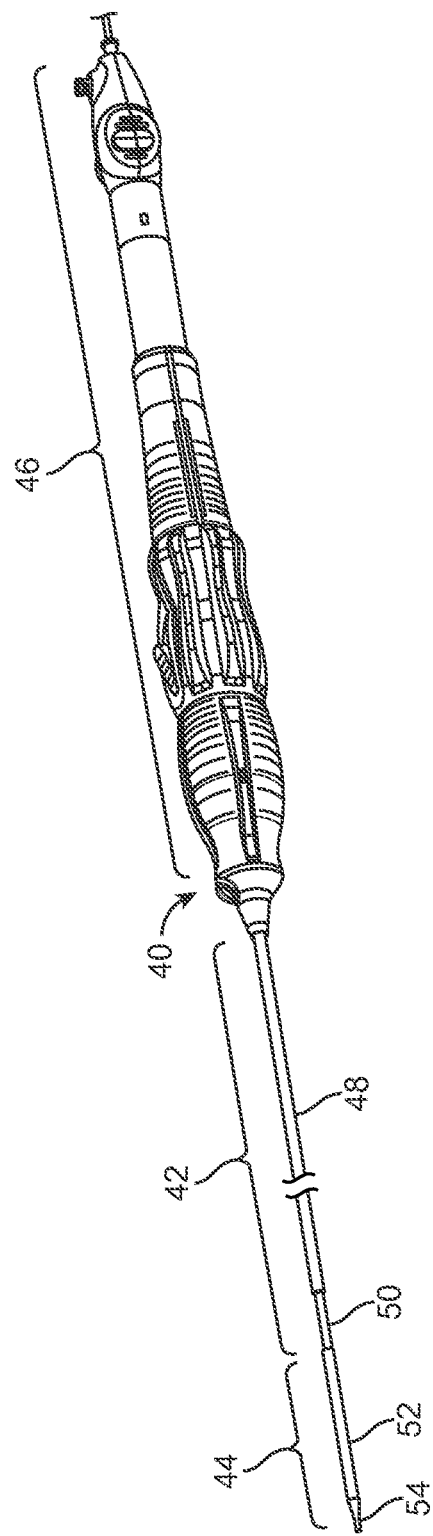
FIG. 3 is a perspective view of a percutaneous stented prosthetic heart valve delivery system in accordance with principles of the present disclosure.

As shown in FIG. 3, delivery system 40 generally comprises a catheter portion 42, a distal deployment portion 44, and a proximal control handle portion 46 by which the deployment portion 44 is effectively controlled. The catheter portion 42 is preferably of a length and size so as to permit a controlled delivery of the deployment portion 44 to a desired implant location of a patient's heart, for example. Preferably, the catheter portion 42 includes features to enhance maneuverability, steerability and advancement of the deployment portion 44 to the point of implantation. The deployment portion 44 provides the means by which a metal frame prosthetic valve can be mounted for delivery to the implantation location and further provides for allowing the expansion of the metal frame prosthetic valve for effective deployment thereof. The control handle portion 46 preferably controls movements as translated to the deployment portion 44 by way of elongate structure of the catheter portion 42. Controlled functionality from the control handle portion 46 is preferably provided in order to permit expansion and deployment of a metal frame prosthetic valve at a desired location, such as a heart valve annulus, and to provide for ease in the delivery and withdrawal of the delivery system through a patient's vasculature.

The catheter portion 42 of the delivery system 40 also preferably comprises an outer stability shaft 48 that is also operatively connected with a distal end of the control handle portion 46 and that surrounds an inner shaft 50 over at least a part of its length. Preferably, the outer stability shaft 48 comprises a lubricous inner layer (such as high density polyethylene HDPE or Polytetrafluoroethylene PTFE), braided stainless steel middle layer with a flexible plastic outer layer, such as comprised of Pebax 7233, or Nylon 12. Preferably, the stability shaft 48 may extend to approximately 80% of the length of the catheter portion 42 of the delivery system as such extends from the control handle portion 46. Such a stability layer 48 facilitates the advancement and steering of the delivery system along a guide wire and through a patient's vasculature by improving the pushability of the delivery system 40. Also, the additional stability shaft 48 adds some stiffness to the proximal end of the catheter portion 42 which translates into a more supportive structure for the catheter portion. This stiffness of stability shaft will minimize the movement of the catheter portion within the anatomy during the deployment of a prosthetic valve. This feature aids the user in making a more accurate deployment because of less movement of the catheter portion within the anatomy during deployment.

Flexible inner shaft 50 is operatively connected with the control handle portion 46 so as to be movable by operation of the handle control portion and that is connected with a sheath 52. Thus, telescopic movement of inner shaft 50 within stability shaft 48 by operation of control handle portion 46 results in the longitudinal translational movement of sheath 52. The control handle portion 46 is designed, among other things, for controlling the advancement and the withdrawal of the sheath 52, and further with respect to an expandable prosthetic heart valve as such can be collapsed onto sheath 52. In another embodiment, catheter portion 42 has no outer stability shaft 48 and no sheath 52, and only has a shaft member 50 with an expandable prosthetic heart valve coupled to a distal end thereof.

A nosecone 54 is provided at a distal end of deployment portion 44 as the leading feature of delivery system 40. The inner shaft 50 also preferably includes an axial lumen (not shown) extending entirely through at least inner shaft 50, sheath 52 and nosecone 54, the purpose of which is for receiving a guide wire, as well known, in order for the delivery system 40 to be guided along a patient's vasculature to an implant location. The guide wire, not shown, may be used in a conventional manner to guide the delivery system along it and with its distal end guided to its desired implant location.

Figure 4:
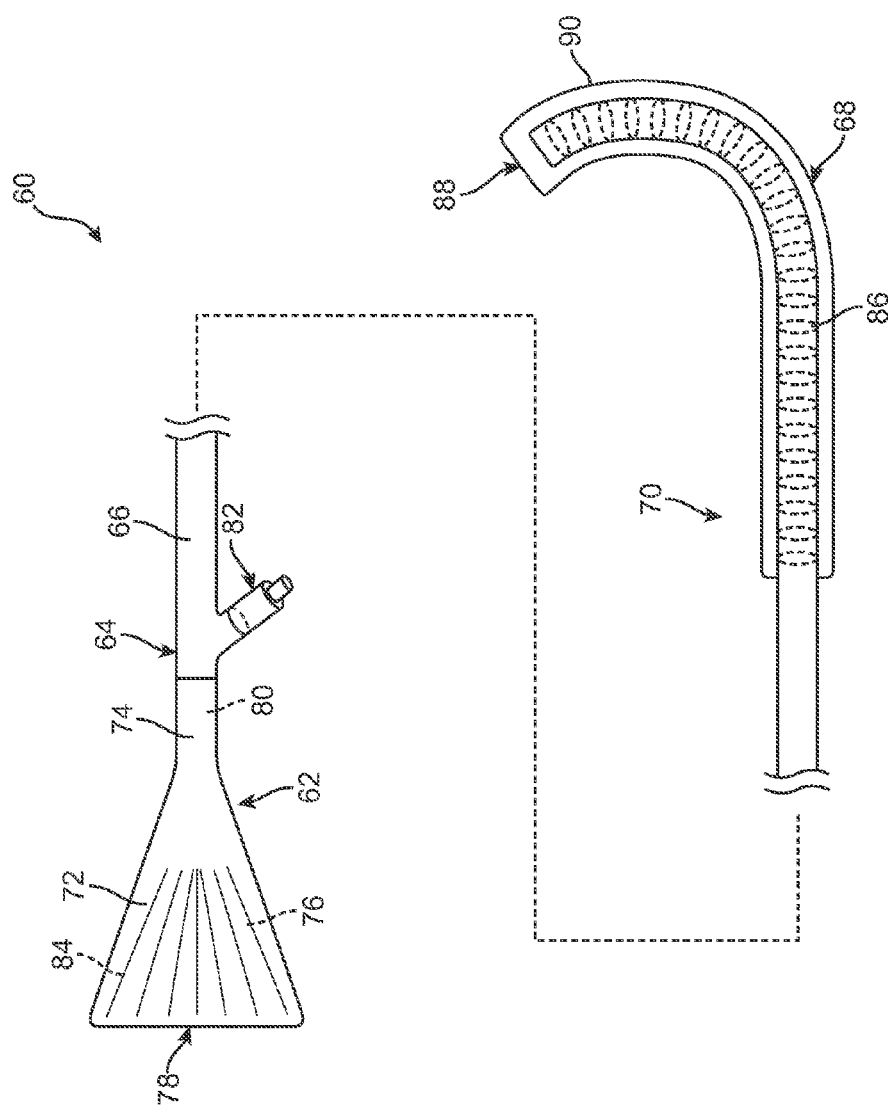
FIG. 4 is an exploded perspective view of a crimping sheath.

FIG. 4 is a perspective view of a crimping sheath 60. Crimping sheath 60 includes an infundibular loading cone 62 coupled to a first or proximal end 64 of a sheath 66 having a lumen extending entirely therethrough. Loading cone 62 is an exemplary embodiment and could be a variety of shapes and sizes of an infundibular cone, or a truncated cone, such as a frustum. A flush port 82 extends from proximal end 64 and is in fluid communication with the lumen of sheath 66. In one embodiment, sheath 66 has an arcuate tip 68 at a second or distal end 70. Arcuate tip 68 also has a lumen, such that loading cone 62, sheath 66 and arcuate tip 68 have lumens which are in fluid communication. In one embodiment, a hemostasis valve (not shown) is disposed between loading cone 62 and flush port 82.

Crimping loading cone 62 includes a funnel portion 72 and a collar 74. In one embodiment, collar 74 is threaded around proximal end 64 of sheath 66. In another embodiment, collar 74 is coupled to proximal end 64 of sheath 66 by a friction fit or snap-on configuration. Funnel portion 72 has an interior surface 76 with a decreasing diameter from an opening 78 of the crimping loading cone 62 to collar 74. Collar 74 also has an interior surface 80 with a constant diameter. Although FIG. 4 shows exemplary interior surfaces of funnel portion 72 and collar 74, other examples of interior surface are possible, such as a continuous interior surface between funnel portion 72 and collar 74 with a decreasing diameter from opening 78 to proximal end 64 of sheath 66. In another embodiment, funnel portion 72 has grooves 84 extending along interior surface 76 of funnel portion 72, such that grooves 84 are aligned substantially parallel to each other and are directed towards collar 74 or generally towards proximal end 64 of sheath 66. Alternatively, groove 784 can be in a spiral configuration on interior surface 76 and directed towards collar 74 or generally towards proximal end 64 of sheath 66 as shown in the embodiment of FIG. 7. Sheath 66 extends distally from collar 74 and is flexible along its length. Although sheath 66 is depicted in FIG. 4 as having a given length relative to crimping loading cone 62, sheath can have any length long enough to extend from the entry point of the patient to the target site, such as the ascending aorta.

In the embodiment shown in FIG. 4, arcuate tip 68 includes a coiled member 86 defining a lumen and opening 88, with coiled member 86 wrapped with polymer tubing 90 and configured in a preformed curve. Although different amounts of deformability are possible, arcuate tip 68 is semi-rigid enough to maintain the preformed curve and yet still deformable when arcuate tip 68 encounters resistance within the patient's vasculature.

In order to prepare a valve prosthesis for implantation, the valve prosthesis can be initially provided in an expanded or uncrimped condition, then crimped or compressed around the catheter until the valve prosthesis diameter is as close to the diameter of the catheter as possible. Various methods and devices are available for crimping the valve onto the catheter, which may include hand-held devices or tabletop devices, for example. Once the valve is crimped onto the catheter by such devices, the delivery device 40 is used with an introducer device (not shown) with the outer stability shaft 48 serving to frictionally isolate the deployment portion 44 from the introducer device. However, in the present disclosure, crimping of the valve 30 onto delivery system 40 is accomplished by using crimping sheath 60.

Figure 5A:
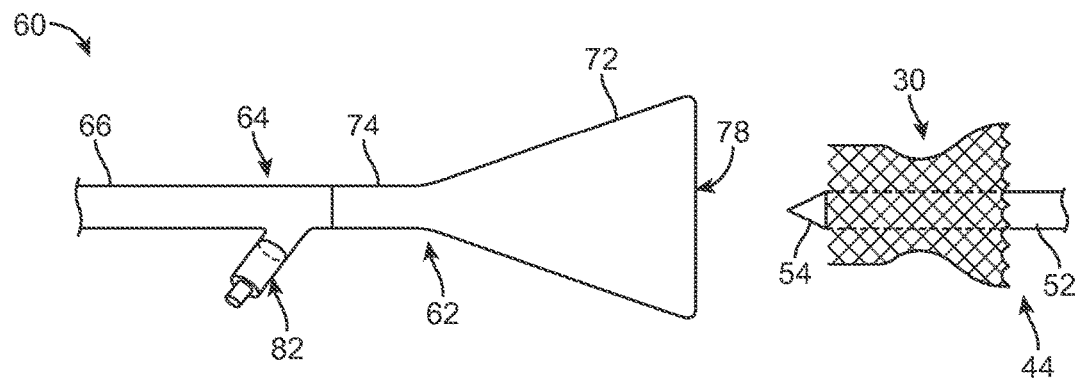
FIG. 5A is a cross-sectional view of a distal portion of the delivery device with an expanded valve prosthesis in close proximity to the crimping sheath.
Figure 5B:
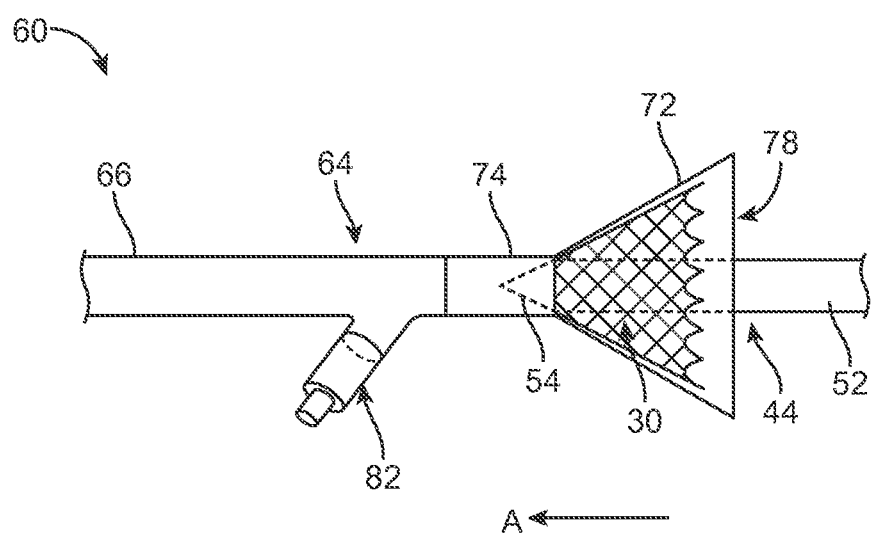
FIG. 5B is a cross-sectional view of a distal portion of the delivery system inserted into the crimping sheath thereby partially crimping the valve prosthesis.
Figure 5C:
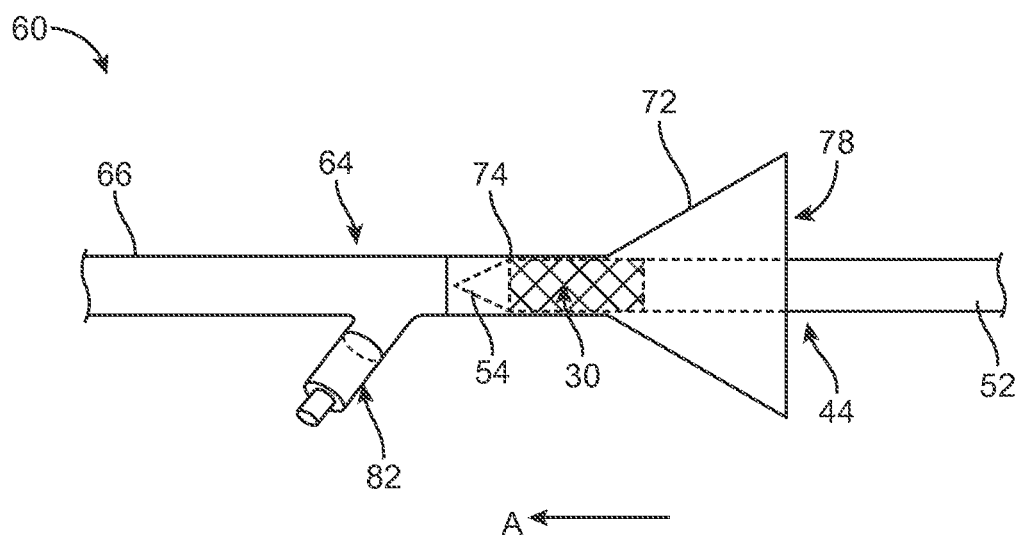
FIG. 5C is a cross-sectional view of a distal portion of the delivery system inserted into the crimping sheath thereby fully crimping the valve prosthesis.
Figure 5D:
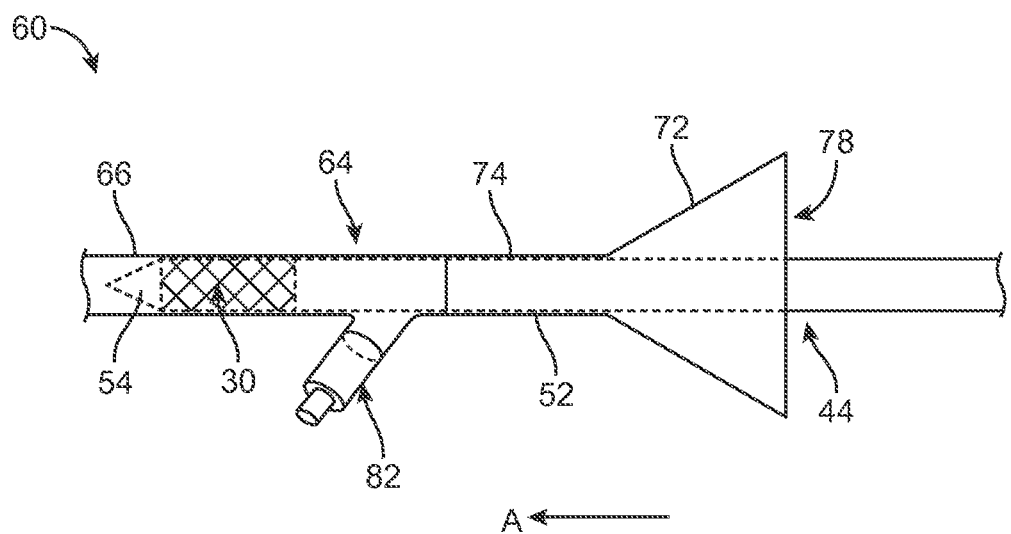
FIG. 5D is a cross-sectional view of a distal portion of the delivery system further advanced into crimping sheath such that the valve prosthesis is compressed.

FIG. 5A is a cross-sectional view showing deployment portion 44 with an expanded valve prostheses 30 coupled to a distal end thereof, and crimping sheath 60. Specifically, valve prostheses 30 is positioned adjacent or in close proximity to the opening 78 of funnel portion 72. FIG. 5B is a cross-sectional view showing partial insertion of valve prostheses 30 into funnel portion 72. In such an arrangement, nosecone 54 may extend into collar 74. Valve prostheses 30 is advanced distally from proximal end 64 of crimping sheath 60 to distal end 70 of crimping sheath 60, as indicated by arrow A. When valve 30 is further advanced into funnel portion 72, the ever decreasing inner diameter of funnel portion 72 gradually compresses the diameter of valve 30 until valve 30 is crimped onto deployment portion 44. As valve 30 transitions between funnel portion 72 into collar 74, the diameter of valve 30 is further compressed until valve 30 is in a crimped configuration onto deployment portion 44, as shown in FIG. 5C. FIG. 5D shows valve 30 in a crimped configuration on deployment portion 44 being advanced along the length of sheath 66 in a direction from proximal end 64 to distal end 70 of sheath 66, as shown by arrow A.

In one embodiment, the diameter of collar 74 is substantially the same diameter as sheath 66. In another embodiment, the diameter of sheath 66 is smaller than the diameter of collar 74. Thus, as valve 30 is further advanced from collar 74 into sheath 66 which has a smaller diameter, valve 30 would be further compressed. In yet another embodiment, the diameter of sheath 66 is variable along its length, such that a smaller diameter of sheath 66 further compresses crimped valve 30 or a larger diameter of sheath 66 allows for expansion of valve 30. In an optional embodiment, sheath 66 may have a lubricious internal coating to help aid the advancement of valve 30 within sheath 66.

Figure 6A:
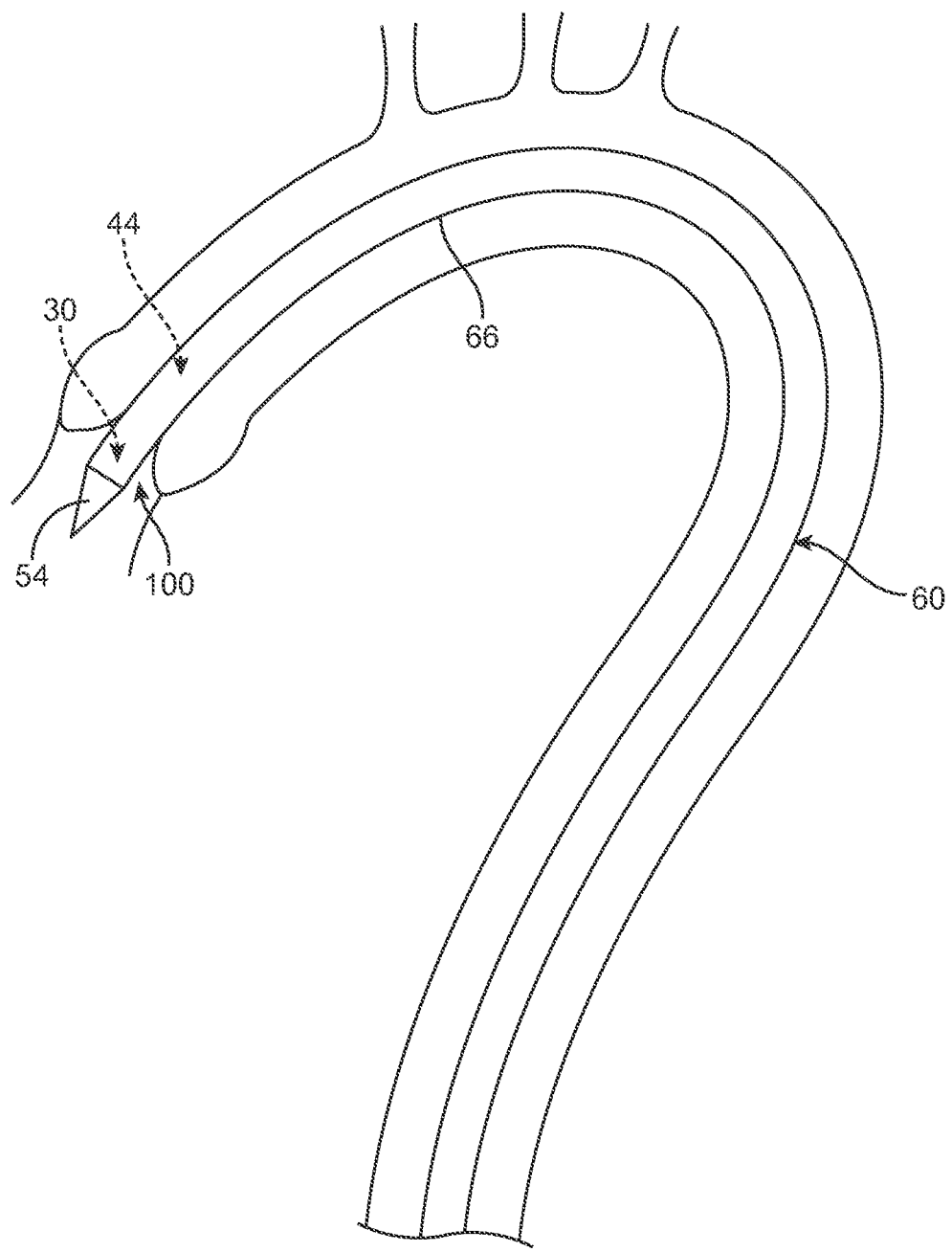
FIGS. 6A-6D illustrate, in simplified form, various steps of another method in accordance with principles of the present disclosure.
Figure 6B:
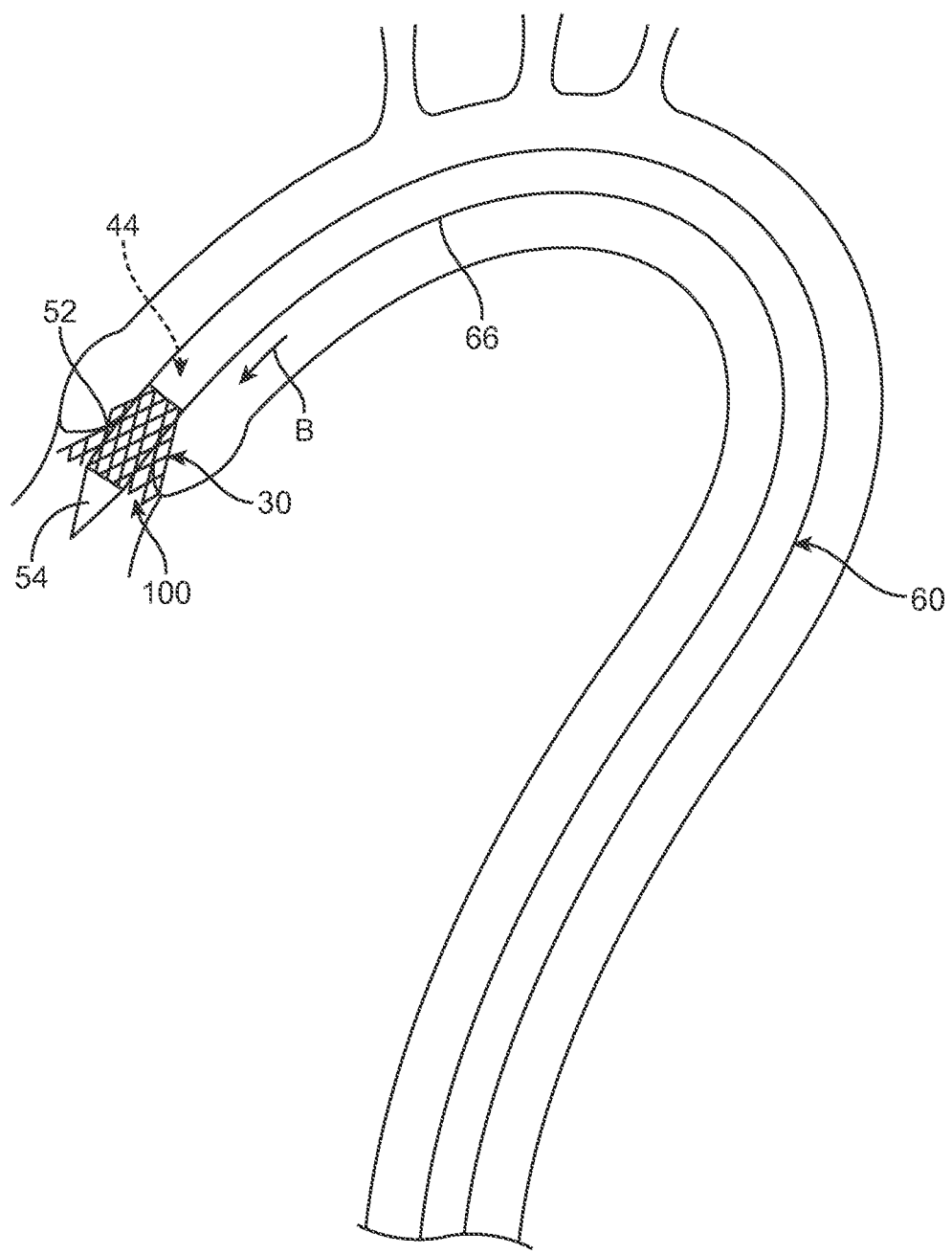
Figure 6C:
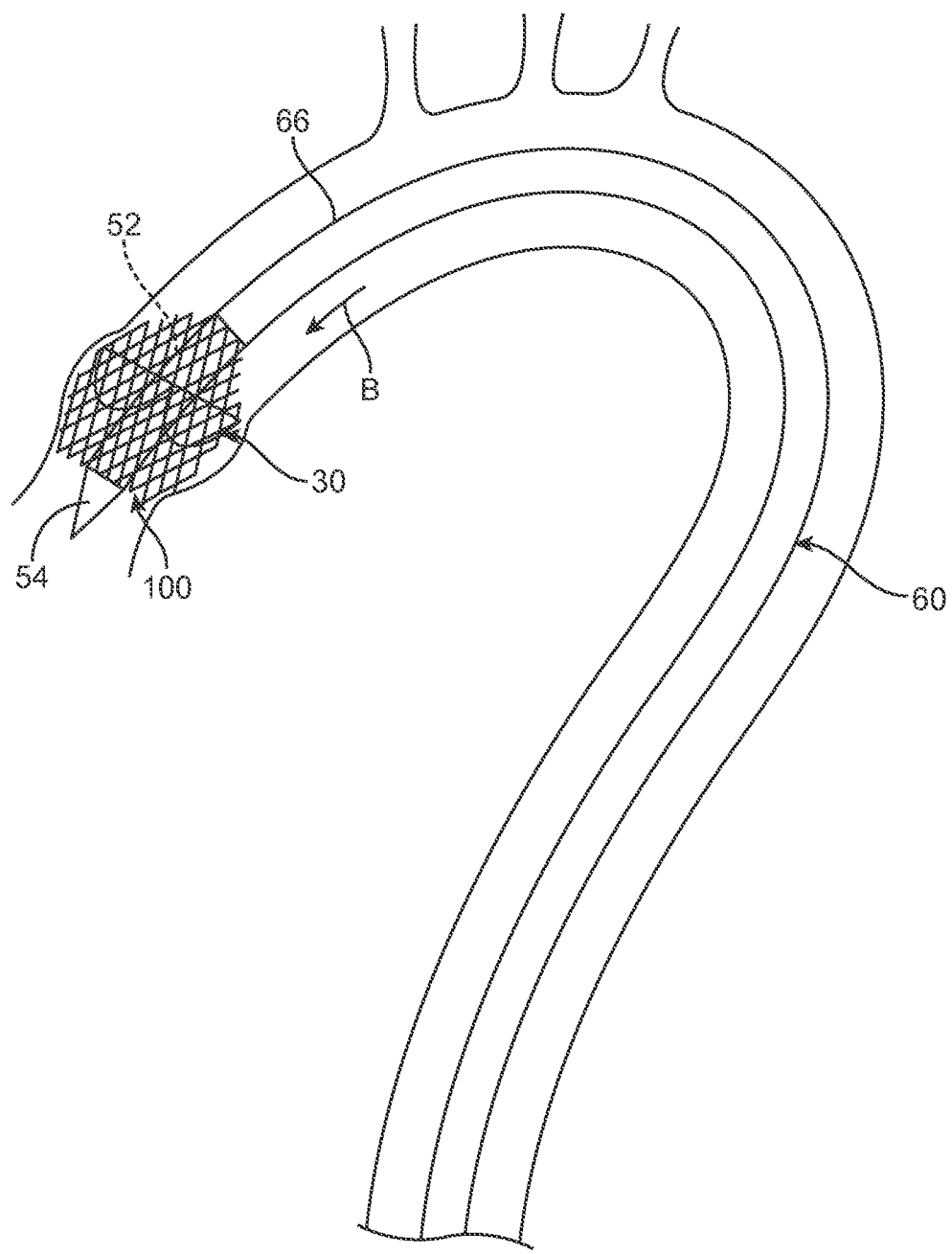
Figure 6D:
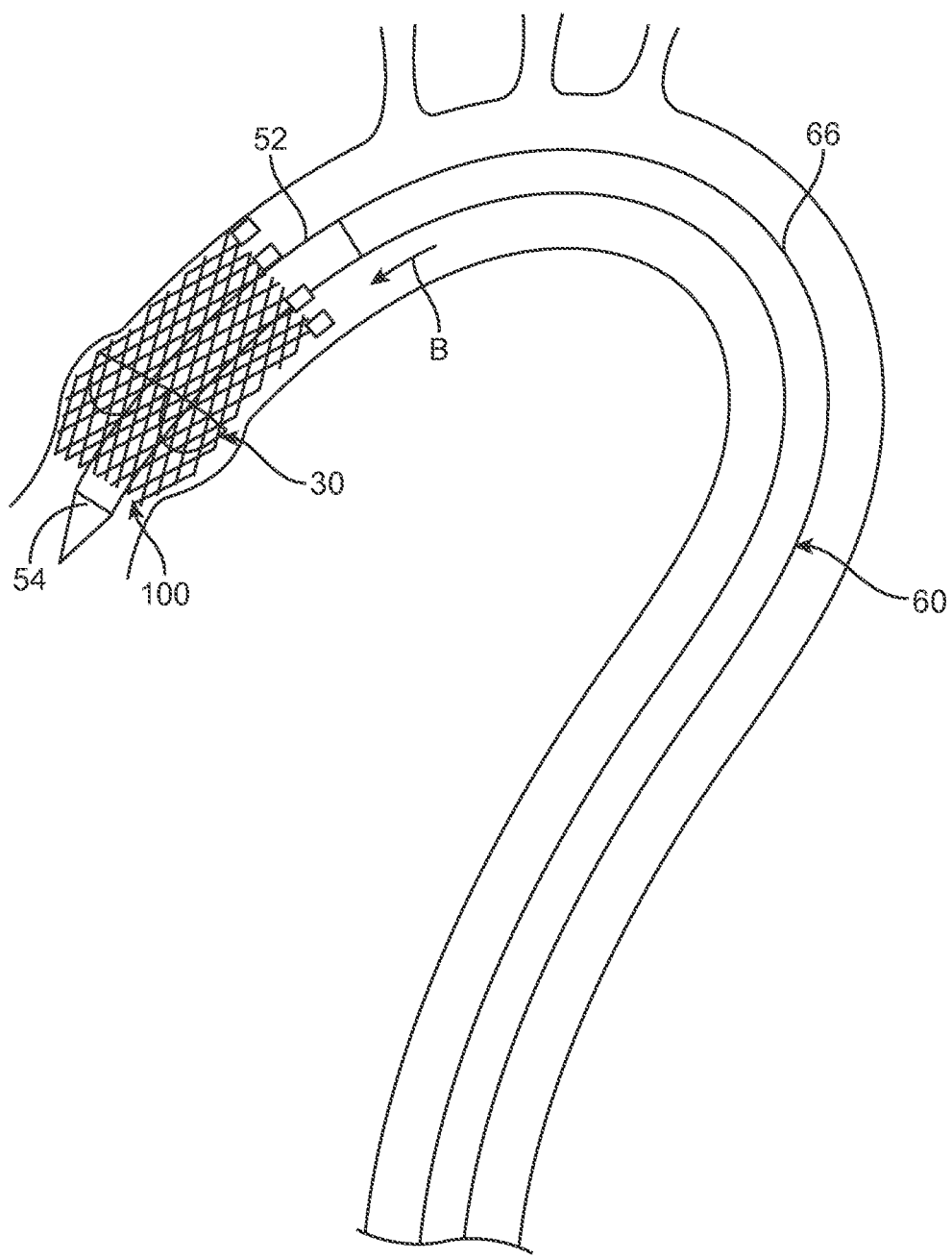

FIGS. 6A-6D illustrate, in simplified form, exemplary use of delivery device 40 and crimping sheath 60. Crimping sheath 60, catheter portion 42 and deployment portion 44 (hidden in FIG. 6A) of delivery device 40 are manipulated to direct prosthetic heart valve 30 (hidden in FIG. 6A) in the compressed arrangement to a treatment site 100 (FIG. 6A). Preferably, crimping sheath 60 includes features to enhance maneuverability, steerability and advancement of crimping sheath to treatment site 100. Deployment portion 44 is then distally advanced (in the general direction of arrow B) past the distal sheath opening 88 thereby allowing the valve 30 to self-expand as shown in FIGS. 6B and 6C. Sheath 66 remains substantially stationary within the patient's vasculature, while deployment portion 44 is further advanced (in the direction of arrow B) and causing valve 30 to further circumferentially expand as shown in FIG. 6C. Due to the nature of the material selection of delivery sheath 66 and deployment portion 44, advancing the deployment portion 44 (with the heart valve coupled thereto) within delivery sheath 66 is characterized by the absence of frictional contact between delivery sheath 66 and deployment portion 44, or alternatively is characterized by the absence of a sliding force being transmitted from delivery sheath 66 onto deployment portion 44. Upon full advancement of deployment portion 44 from crimping sheath 60 (FIG. 6D), valve 30 is shown to be positioned and seated at the treatment site 100. In another embodiment, deployment portion 44 remains stationary and crimping sheath 60 is proximally withdrawn in a direction opposite to arrow B thereby allowing valve 30 to self-expand. Crimping sheath 60 and methods of delivery device 40 provide a marked improvement over previous designs. By isolating the delivery sheath from an introducer device, potential complications associated with previous configurations are overcome.

The foregoing description has been presented for purposes of illustration and enablement, and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

Although the present disclosure has been described with reference to preferred embodiments, workers skilled in the art will recognize that changes can be made in form and detail without departing from the spirit and scope of the present disclosure. For example, the delivery systems shown and described herein can be modified for delivery of balloon-expandable stented prosthetic heart valves, within the scope of the present disclosure. That is to say, delivering balloon-expandable stents to an implantation location can be performed percutaneously using modified versions of the delivery devices of the present disclosure. In general terms, this includes providing a transcatheter assembly that can include a delivery sheath and/or additional sheaths as described above. The devices would further include a delivery catheter, a balloon catheter, and/or a guide wire. A delivery catheter used in this type of delivery device defines a lumen within which the balloon catheter is received. The balloon catheter, in turn, defines a lumen within which the guide wire is slidably disposed. Further, the balloon catheter includes a balloon that is fluidly connected to an inflation source. With the stented valve mounted to the balloon, the transcatheter prosthetic valve is delivered through a percutaneous opening in the patient via the delivery device. Once the stented prosthetic heart valve is properly positioned, the balloon catheter is operated to inflate the balloon, thus transitioning the stented prosthesis to an expanded arrangement.

What is claimed is:

1. A method for restoring a defective heart valve of a patient, the method comprising:
   providing a delivery device having a distal deployment portion and a proximal control handle portion by which the distal deployment portion is effectively controlled, the distal deployment portion having a prosthetic heart valve coupled thereto, the prosthetic heart valve being radially self-expandable;
   providing a delivery sheath defining a lumen, the delivery sheath having a distal portion defining an opening and a loading cone coupled to a proximal end of the delivery sheath, the loading cone defining an opening in fluid communication with the lumen;
   establishing an access portal to a bodily lumen of the patient with an introducer device;
   inserting the delivery sheath into the bodily lumen through the introducer device;
   manipulating the delivery sheath through the patient's vasculature and into the defective heart valve;
   inserting the delivery device into the loading cone, wherein the prosthetic heart valve is compressed until the prosthetic heart valve is in a crimped arrangement,
   advancing the delivery device distally through the delivery sheath toward the opening of the delivery sheath; and
   advancing the delivery device past the opening of the delivery sheath by sliding the delivery device relative to the delivery sheath to release the prosthetic heart valve from the delivery sheath and permit the prosthetic heart valve to self-expand into engagement with the defective heart valve.

2. The method of claim 1, wherein the loading cone has a funnel portion and a collar extending therefrom, wherein the collar is coupled to the proximal end of the delivery sheath, and the lumen of the delivery sheath has a smaller diameter than the collar.

3. The method of claim 1, wherein the lumen of the delivery sheath has a decreasing diameter from the proximal end to the opening.

4. The method of claim 1, wherein the distal portion is deformable and configured in a preformed curve such that when manipulating the delivery sheath through the patient's vasculature, the distal portion deforms when a distal tip thereof encounters resistance with the patient's vasculature.

5. The method of claim 1, wherein advancing the delivery device with the prosthetic heart valve coupled thereto is characterized by the absence of frictional contact between the delivery sheath and the delivery device.

6. The method of claim 1, wherein advancing the delivery device with the prosthetic heart valve coupled thereto is characterized by the absence of a sliding force being transmitted from the delivery sheath onto the delivery device.

* * * * *